United States Patent
Ekey

Patent Number: 5,980,499
Date of Patent: Nov. 9, 1999

[54] POST SURGICAL DRAIN RECEPTACLE SUPPORT SYSTEM

[76] Inventor: Barbara Norton Ekey, 393 Keller Rd., Warren, Pa. 16365

[21] Appl. No.: 09/092,602

[22] Filed: Jun. 5, 1998

[51] Int. Cl.[6] .................................. A61F 5/44; A61F 5/00
[52] U.S. Cl. .......................... 604/345; 604/179; 224/663; 224/682
[58] Field of Search .................. 604/345, 327, 604/179; 224/682, 663, 676

[56] References Cited

U.S. PATENT DOCUMENTS

| | | | |
|---|---|---|---|
| D. 128,066 | 7/1941 | Haubein . | |
| D. 277,810 | 3/1985 | Pickens | D2/383 |
| D. 319,732 | 9/1991 | Gumbs | D3/100 |
| D. 365,928 | 1/1996 | Sauer | D3/224 |
| 1,968,767 | 7/1934 | Howard | 221/23 |
| 2,699,782 | 1/1955 | Chester | 128/295 |
| 4,548,375 | 10/1985 | Moss | 248/205.2 |
| 4,819,846 | 4/1989 | Hannemann | 224/240 |
| 4,923,105 | 5/1990 | Snyder | 224/255 |
| 5,026,362 | 6/1991 | Willett | 604/345 |
| 5,032,118 | 7/1991 | Mason | 604/349 |
| 5,135,519 | 8/1992 | Helmer | 604/332 |
| 5,259,541 | 11/1993 | Reese | 224/226 |
| 5,643,233 | 7/1997 | Turner | 604/332 |
| 5,651,777 | 7/1997 | Walters | 604/345 |
| 5,716,344 | 2/1998 | Kiel | 604/174 |

*Primary Examiner*—John G. Weiss
*Assistant Examiner*—Catherine Cogut
*Attorney, Agent, or Firm*—Thompson Hine & Flory LLP

[57] ABSTRACT

A drainage receptacle support system for use by a post operative patient. The support device includes an adjustable belt and a plurality of pockets for individually receiving a drainage receptacle. A loop is provided on the back of the pockets for slidably receiving the belt, so that the pockets may be positioned directly underneath an insertion point for the drainage tubes. The loop is positioned so that the pockets are held in a generally upright position. Preferably the support device is lightweight and washable, and the pockets and the loop include padding to distribute the weight of the receptacle.

31 Claims, 3 Drawing Sheets

5,980,499

POST SURGICAL DRAIN RECEPTACLE SUPPORT SYSTEM

BACKGROUND OF THE INVENTION

This invention relates to post surgical drain receptacle supports, and more particularly to drain receptacle supports to be worn about the abdomen of a patient.

Following certain types of surgery, especially surgery involving the removal of tissue, the resulting body cavity may fill with fluid. Examples of such surgery include mastectomies and lumpectomies with auxiliary nodal dissection, which involved removal of lymph nodes under the arm. The removal of the large amount of tissue in such procedures creates a cavity, and as a result, the remaining lymph nodes secrete fluid which collects in the cavity. To relieve swelling and infection that may occur if the fluid is left in the body, a drainage tube is inserted through the surgical incision into the cavity. Such drain tubes typically have perforated ends through which fluid enters the tube from the cavity. Drainage of such fluid provides the further advantage of creating a negative pressure in the body cavity, thereby holding the skin against the muscle until it heals. When such operations require tissue removal from multiple sites, post operative treatment will utilize multiple tubes and bottles, each associated with a separate incision.

The drainage tubes are connected to receptacles, such as plastic bottles, for collecting the fluid. Depending on the surgery and the amount of fluid buildup expected, the number of drainage tubes and receptacles utilized can vary from as few as one to as many as four. However many drainage tubes are utilized, the managing of the tubes and their associated receptacles pose certain problems. In the past, it was common to pin the receptacles to clothing worn by the patient or to the bandage for the incision itself. While not very comfortable, this procedure was somewhat effective in the hospital where an open gown was worn, thereby easing the ability of the patient to accommodate basic bodily functions. Furthermore, the awkwardness and discomfort is increased with multiple sets of bottles and tubes. In addition, outside of the hospital, where patients wear standard, relatively constricting clothes, it is not practicable to use such means to receive drain bottles. Accordingly, with the advent of insurance company mandates on shorter hospital stays for many types of surgeries, these types of problems have become more prevalent.

U.S. Pat. No. 5,643,233 to Turner attempts to address some of these problems by providing a single large pouch to be worn on a belt which extends about the waist of a post operative patient to support fluid drainage receptacles. The pouch of that device includes a pouch extension, an elongate loop of fabric which receives the belt and supports the pouch so that the pouch opening hangs down below the belt and deflects in an angular position when the lip of the pouch is pulled away from the wearer, thereby allowing easy access to the interior of the pouch. While the Turner patent resolves some of the problems associated with prior art post operative drainage receptacle supports, it is not completely effective. For example, the Turner device cannot hold a number of drainage receptacles individually in separate, secured positions about a patient's body in locations which avoid tangling of the drainage tubes.

Accordingly, there exists a need for a lightweight support device for drainage receptacles to be worn by post operative patients which comfortably secures the drainage receptacles against a wearer, which can be worn under clothing, which facilitates draining of the receptacles, and which can be positioned in a manner to avoid tangling and stress on the drain tubes.

SUMMARY OF THE INVENTION

The present invention is a post surgical drain receptacle support system which securely supports a number of drainage receptacles and can be worn comfortably by a post operative patient. The present invention includes an adjustable belt and at least one pocket shaped to receive and individual drain receptacle, typically a plastic bottle, and having a loop for receiving the adjustable belt. The pocket preferably is positioned on the belt directly underneath the point of insertion for the drainage tube in the incision, thereby minimizing stretching of the tube, stressing the incision and the chance of entanglement with another tube. The lip of the cavity of the pocket is held at least even with the belt, thereby securing the pocket close to the body of the wearer. Preferably, the pocket of the present invention is made from a lightweight, non-abrasive, washable fabric having padding positioned between the bottle and the body of the wearer.

If a number of incisions are made in an operation, the system can be expanded to accommodate a number of pockets, each individually positionable on the belt and corresponding to a like number of drainage bottles. Such a system can be adjusted easily by a patient.

Accordingly, it is an object of the present invention to provide a support system for post operative drainage receptacles to be worn by patients which individually supports the drainage receptacles in a position to avoid the tangling of and stretching of the drainage tubes; a system which can be adapted to support a number of drainage receptacles; a system which facilitates drainage of incisions into receptacles; a system which can be worn under clothing, and is lightweight, washable and comfortable.

Other objects and advantages of the present invention will be apparent from the following description, the accompanying drawings and the appended claims.

DETAILED DESCRIPTION

Figure 1:
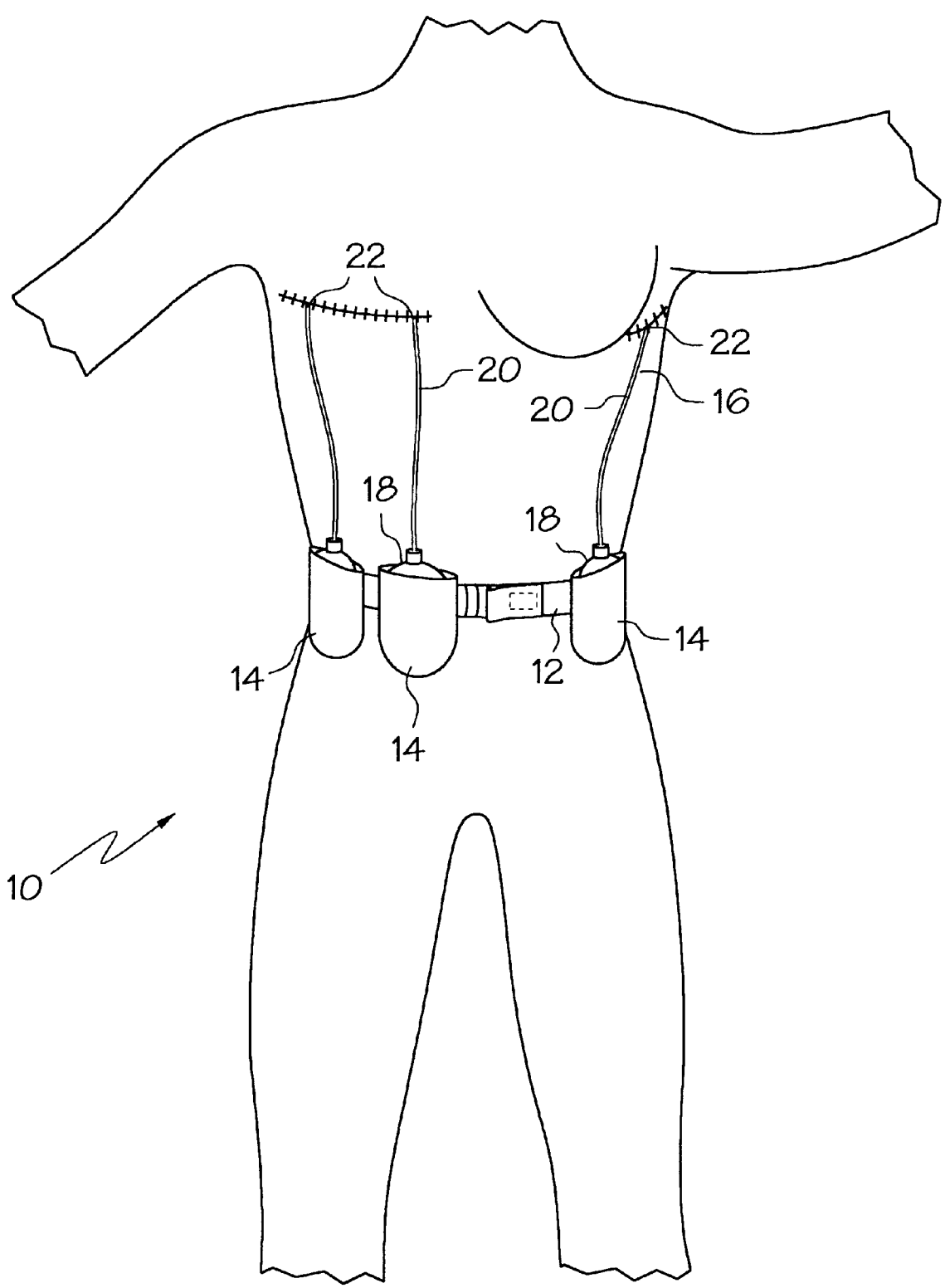
FIG. 1 is a front perspective view of the drainage receptacle support system of the present invention, shown worn by a post operative patient.

As shown in FIG. 1, in accordance with a preferred embodiment of the present invention, a support system for a fluid drainage receptacle, generally designated 10, includes an adjustable belt 12 and a plurality of pockets 14. The belt 12 is shaped to be worn around the abdomen of a patient 16. While a human patient 16 is shown in FIG. 1, the system 10 may be employed on animals, such as horses and cows as well, and therefore are to be included with the term "patient" as used herein. The pockets 14 are shaped to slidably receive adjustable belt 12 and to receive an individual drainage receptacle, such as a plastic bottle 18. Drainage tubes 20 are inserted in incision 22 on a patient 16 an extend downwardly into bottles 18.

Figure 2:
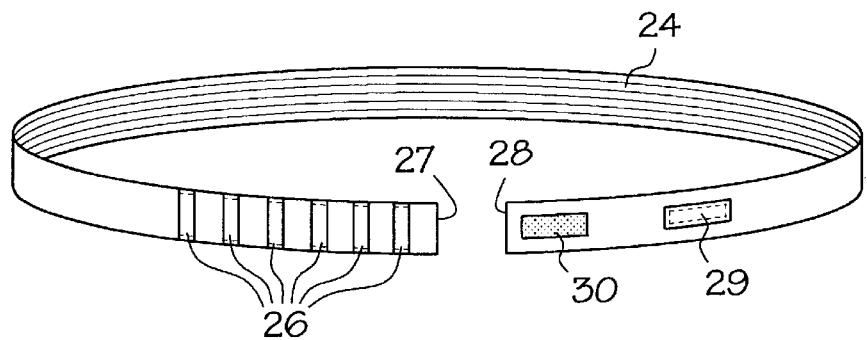
FIG. 2 is a front perspective view of the belt of the support system of FIG. 1.

As best shown in FIG. 2, the adjustable belt 12 preferably is made from an elastic fabric material and has a non-abrasive facing 24 attached to the inside portion facing the wearer. Fabric adjustment loops 26 are attached to the outside of one end 27 of the belt 12 in a spaced array. Complementary strips 29, 30 of hook and loop material are attached to the opposite end 28 of the belt 12 spaced a distance apart from each other.

Figure 3:
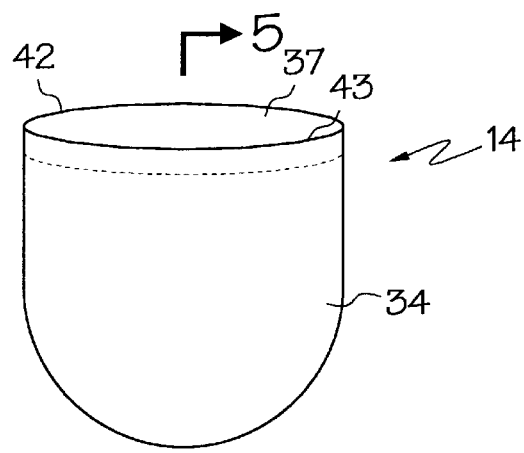
FIG. 3 is a front perspective view of the pocket of the support system, of FIG. 1.
Figure 4:
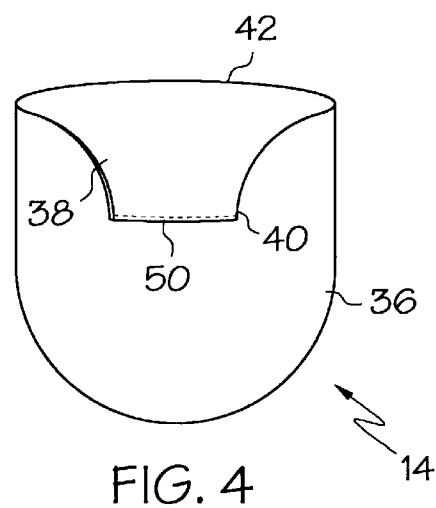
FIG. 4 is a rear perspective view of the pocket of the support system of FIG. 1.
Figure 5:
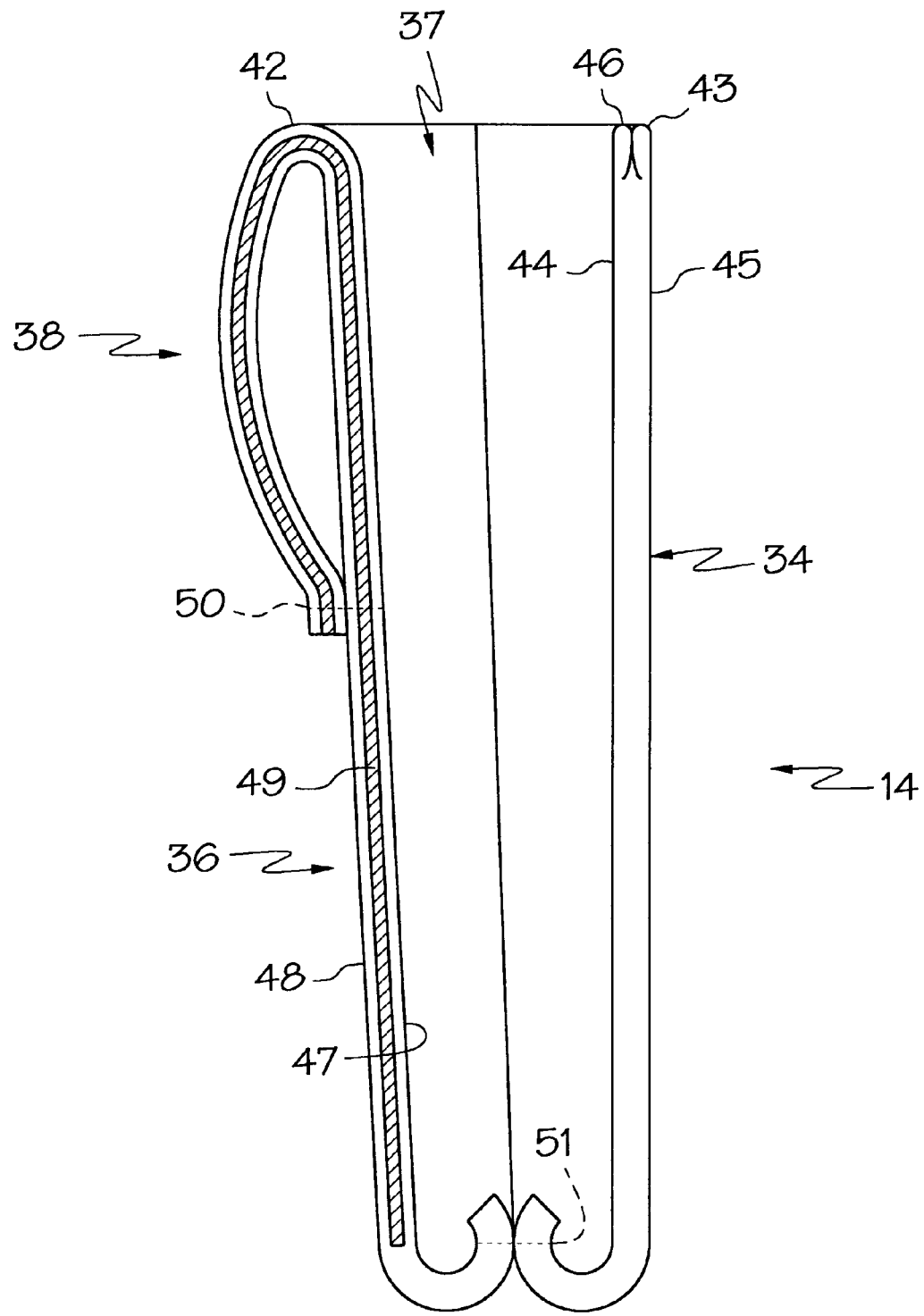
FIG. 5 is a section of the pocket of the present invention, taken at line 5—5 of FIG. 3.

As shown in FIGS. 3, 4 and 5, the pocket 14 of the present invention includes a front panel 34 and a back panel 36, preferably made from a soft, non-abrasive material such as cotton. The front and back panels 34, 36 form an internal cavity 37 shaped to receive a surgical drainage receptacle 18 (see FIG. 1). The back panel 36 includes a loop 38 shaped to slidably receive the belt 12 (see FIG. 2). Preferably, the loop 38 is unitary with the back panel 36 and is formed by turning an edge 40 of the back panel 38 over upon the back panel 36 and attaching it to itself thereby forming the loop. The top 42 of the loop is even with the top 43 of the front panel 34.

As shown in FIG. 5, the front panel 34 is made of inner and outer layers 44, 45 of fabric stitched together at 46 at the top 43. The back panel 38 includes inner and outer layers 47, 48 of fabric, which enclose a panel 44 of foam. Layer 47, 48 of fabric, and foam panel 49, fold over on themselves to form loop 38, secured by stitching 50. The front and back panels 34, 36 are joined by stitching 51 which extends about the inner position of the pocket 14.

The loop 38 is shaped to hold the pocket 14 firmly against the belt 12 such that the belt is below or even with the top 43 of the front panel 34 (the top of the loop comprises the top of the back panel 36), thereby insuring that a receptacle 18 carried in the pocket 14 will be held in a substantially upright position. Since the pocket 14 is held firmly against the belt 12, the pocket is held firmly against the patient, which minimizes movement of the pocket relative to the patient. The foam panel 49 distributes pressure from a receptacle 18 carried in the internal cavity 32 of the pocket 14 about the back panel 36 and loop 38, thus adding to the comfort of the system 10.

The operation of the drainage receptacle support device of the present invention is as follows. A number of pockets 14 corresponding to a like number of drainage receptacles 18 are selected and slidably mounted on the belt 12. The belt 12 is then placed around the abdomen of post operative patient 16 and end 28 of the belt 12 having a hook strip 29 and a loop strip 30 of material attached thereto is fed through a selected one or the adjustment loops 26 providing the most comfortable fit for the belt 12. The end of the belt is then turned upon itself so that the complementary strips 29, 30 of hook and loop material engage each other thereby fastening the belt. Any portion of the belt 12 not being used may be cut off and discarded if desired.

Next, the pockets 14 may be positioned on the belt 12 in a least restrictive, most comfortable, position for the post operative patient 16 in order to avoid tugging on and tangling of the drainage tubes 20, which typically is directly underneath each corresponding insertion point 22. Drain bottles 18 are each placed in an individual corresponding pocket 14 providing the post operative patient with support. The receptacles 14 may be easily removed for emptying, and the receptacle support device 10 may be washed as necessary.

While the form of the apparatus herein described constitutes a preferred embodiment of the invention, it is to be understood that the invention is not limited to the precise form of apparatus, and that changes may be made therein without departing from the scope of the invention.

What is claimed is:

1. For use with a drainage receptacle connected to a post-operative surgery patient, a support device comprising:
    a belt shaped to be worn about the abdomen of a wearer;
    a pocket having an internal cavity shaped to receive a surgical drainage receptacle, said pocket having a back panel made of a relatively non-abrasive material and having padding positioned in between said cavity and a wearer such that pressure from a receptacle carried in said cavity is distributed about said back panel, and said back panel also having a loop for slidably receiving said belt, said loop being shaped to hold said pocket against said belt such that said belt is below an upper surface of said back panel, wherein said pocket is held against a wearer such that a carried receptacle is held in a substantially upright position.

2. The support device of claim 1 wherein said loop is made from a relatively non-abrasive material and having padding positioned in between said pocket and a wearer such that pressure from said belt is distributed about said loop.

3. The support device of claim 2 wherein said loop is unitary with said back panel.

4. The support device of claim 1 wherein said pocket includes a front panel.

5. The support device of claim 4 wherein said front panel defines said cavity with said back panel.

6. The support device of claim 4 wherein said front panel includes an upper edge positioned substantially even with an upper edge of said back panel.

7. The support device of claim 6 wherein said upper edges of said front and back panels define a mouth of said cavity.

8. The drainage receptacle support device of claim 7 wherein said loop is shaped such that an upper edge thereof is even with an upper edge of said front panel.

9. The support device of claim 4 wherein said front panel is made of a relatively non-abrasive material.

10. The support device of claim 1 wherein said pocket is shaped to retain no more than a single receptacle.

11. The support device of claim 10 further comprising a plurality of said pockets attached to said belt.

12. The support device of claim 1 wherein said belt is made of an elastic material.

13. The support device of claim 1 wherein said belt includes a non-abrasive facing.

14. The support device of claim 1 wherein said back panel is made from a fabric having a foam lining.

15. The support device of claim 1 wherein said belt is adjustable.

16. The support device of claim 15 wherein said belt includes a plurality of loops attached in a spaced array to an end thereof, and complementary strips of hook and loop material attached to an opposite end of said belt, wherein said opposite end can be inserted though a selected one of said loops and can be folded over on itself to engage said strips of hook and loop material, thereby fastening said belt.

17. The support device of claim 1 wherein said cavity is shaped to hold no more than a single mastectomy drain bottle.

18. The drainage receptacle support device of claim 1 wherein said pocket weighs approximately one half an ounce.

19. For use with a drainage receptacle by a post-operative surgery patient, a support device comprising:
    a belt shaped to be worn about the abdomen of a wearer made of an elastic material having a non-abrasive surface, said belt having a plurality of loops attached in a spaced array to an end thereof, and complementary strips of hook and loop material attached to an opposite end of said belt, wherein said opposite end can be inserted though a selected one of said loops and can be folded over on itself to engage said strips of hook and loop material, thereby fastening said belt;

at least one pocket shaped to retain no more than a single mastectomy drainage bottle having an internal cavity, said pocket having a front panel and a back panel having upper edges positioned substantially evenly, said panels defining said cavity and said edges defining a mouth for said cavity, and a loop made of a relatively non-abrasive material having a top surface positioned substantially evenly with said panel upper edges for slidably receiving said belt, said loop being unitary with said back panel, and both said loop and said back panel having padding positioned in between said cavity and a wearer such that pressure from a receptacle carried in said cavity is distributed about said loop and said back panel, said loop shaped to hold said pocket against said belt such that said belt is below said upper edge of said back panel, wherein said pocket is held against a wearer such that a carried receptacle is held in a substantially upright position.

20. A method for supporting a post operative surgical drainage receptacle comprising the steps of:

selecting an adjustable belt shaped to be worn about the abdomen of a wearer;

selecting at least one pocket, said pocket having a back panel made of a relatively non-abrasive material and having padding positioned in between said cavity and a wearer such that pressure from a receptacle carried in said cavity is distributed about said back panel, and said back panel also having a loop for slidably receiving said belt, said loop being shaped to hold said pocket against said belt such that said belt is below an upper surface of said back panel, wherein said pocket is held against a wearer such that a carried receptacle is held in a substantially upright position;

slidably mounting said pocket on said belt;

fastening said belt around the abdomen of a post operative patient; and inserting a surgical drainage receptacle into said pocket.

21. The method of claim 20 wherein said pocket selecting step includes the step of selecting a number of pockets corresponding to a like number of surgical drainage receptacles attached to the wearer, each having openings shaped to receive a single one of said receptacles.

22. The method of claim 21 further comprising the step of adjusting the placement of said pockets to a comfortable and least restrictive location.

23. The method of claim 21 further comprising the step of adjusting the placement of said pockets to a position directly under an insertion point for a drainage tube.

24. The method of claim 21 wherein said pocket selecting step includes the step of selecting pockets made from a non-abrasive material.

25. The method of claim 20 wherein said belt selecting step includes the step of selecting a waist belt made from an elastic material.

26. The method of claim 20 wherein said belt selecting step includes the step of selecting a belt having a non-abrasive facing.

27. The method of claim 20 wherein said pocket selecting step includes the step of selecting pockets made from a foam lined fabric.

28. The method of claim 20 wherein said pocket selecting step includes the step of selecting pockets that are approximately the size of a dress shirt pocket.

29. The method of claim 20 wherein said pocket selecting step includes the step of selecting pockets that can be appropriately worn under clothing.

30. The method of claim 20 wherein said belt selecting step includes the step of selecting a belt having a plurality of loops attached in a spaced array to a first end of said belt, and strips of hook and loop material attached to a second end of said belt, wherein said belt second end can be inserted though one of said loops on said belt first end, and be folded over on itself thereby engaging said hook and loop material and fastening said belt.

31. The method of claim 20 wherein said pocket selecting step includes the step of selecting pockets designed to receive surgical drainage receptacles worn by post-operative mastectomy patients.

* * * * *